United States Patent [19]

Fuchs et al.

[11] 4,279,923

[45] Jul. 21, 1981

[54] COMBATING PESTS WITH 3-(2,3-DICHLORO-3,3-DIFLUORO-PROP-1-EN-1-YL)-2,2-DIMETHYL-CYCLO-PROPANECARBOXYLIC ACID FLUORO-BENZYL ESTERS

[75] Inventors: Rainer Fuchs, Wuppertal; Klaus Naumann, Cologne; Reinhard Lantzsch, Leverkusen; Hermann Hagemann; Ingeborg Hammann, both of Cologne; Bernhard Homeyer, Leverkusen; Wolfgang Behrenz, Overath; Wilhelm Stendel, Wuppertal, all of Fed. Rep. of Germany

[73] Assignee: Bayer Aktiengesellschaft, Leverkusen, Fed. Rep. of Germany

[21] Appl. No.: 185,836

[22] Filed: Sep. 10, 1980

[30] Foreign Application Priority Data

Oct. 2, 1979 [DE] Fed. Rep. of Germany ....... 2939913

[51] Int. Cl.³ ................... A01N 53/00; C07C 69/743; C07C 121/75
[52] U.S. Cl. ............... 424/304; 260/465 D; 560/124; 424/305
[58] Field of Search ................... 260/465 D; 560/124; 424/304, 305

[56] References Cited

U.S. PATENT DOCUMENTS 4,183,948  1/1980  Huff ........................................ 424/304

Primary Examiner—Dolph H. Torrence
Attorney, Agent, or Firm—Sprung, Felfe, Horn, Lynch & Kramer

[57] ABSTRACT

3-(2,3-Dichloro-3,3-difluoro-prop-1-en-1-yl)-2,2-dimethyl-cyclo-propanecarboxylic acid fluoro-benzyl esters of the formula

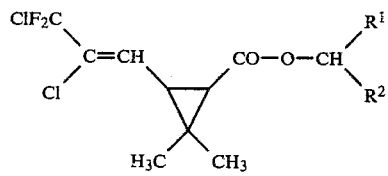

in which $R^1$ represents hydrogen, cyano, alkyl with up to 4 carbon atoms, alkenyl with up to 4 carbon atoms or alkynyl with up to 4 carbon atoms, and $R^2$ represents a phenyl radical which is substituted by fluorine and/or optionally fluorine-substituted phenoxy, with the proviso that the radical $R^2$ in total contains at least one fluorine substituent, which possess pesticidal activity.

9 Claims, No Drawings

COMBATING PESTS WITH 3-(2,3-DICHLORO-3,3-DIFLUORO-PROP-1-EN-1-YL)-2,2-DIMETHYL-CYCLO-PROPANECARBOXYLIC ACID FLUORO-BENZYL ESTERS

The invention relates to certain new 3-(2,3-dichloro-3,3-difluoro-prop-1-en-1-yl)-2,2-dimethyl-cyclo-propanecarboxylic acid fluoro-benzyl esters, to a process for their preparation and to their use in agents for combating pests, in particular as insecticides and acaricides.

It is known that certain substituted cyclopropanecarboxylic acid esters, for example 3-(2-methyl-prop-1-en-1-yl)- and 3-(2,2-dichloro-vinyl)-2,2-dimethyl-cyclopropane-carboxylic acid 3-phenoxybenzyl ester (Phenothrin and Permethrin) have an insecticidal and acaricidal action (see British Pat. Nos. 1,243,858 and 1,413,491).

However, the action of these compounds is not always satisfactory, especially in the case of low concentrations of active compound and when small amounts are applied.

The present invention provides, as new compounds, the 3-(2,3-dichloro-3,3-difluoro-prop-1-en-1-yl)-2,2-dimethyl-cyclopropanecarboxylic acid fluoro-benzyl esters of the general formula

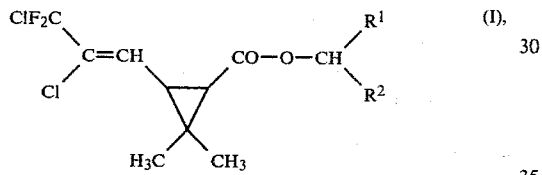

in which
R¹ represents hydrogen, cyano, alkyl with up to 4 carbon atoms, alkenyl with up to 4 carbon atoms or alkynyl with up to 4 carbon atoms, and
R² represents a phenyl radical which is substituted by fluorine and/or by optional fluorine-substituted phenoxy, with the proviso that the radical R² in total contains at least one fluorine substituent.

The invention also provides a process for the preparation of a compound of the formula (I) in which 3-(2,3-dichloro-3,3-difluoro-prop-1-en-1-yl)-2,2-dimethylcyclopropanecarboxylic acid, of the formula

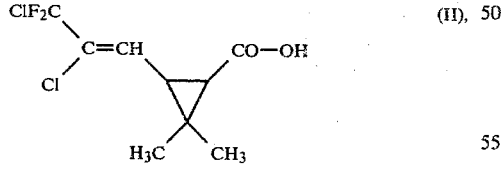

or a reactive derivative thereof, is reacted with a benzyl alcohol of the general formula

in which
R² and R³ have the meanings indicated above, or with a reactive derivative thereof, if appropriate in the presence of an acid acceptor and/or a catalyst and if appropriate using a diluent.

The 3-(2,3-dichloro-3,3-difluoro-prop-1-en-1-yl)-2,2-dimethyl-cyclopropanecarboxylic acid fluoro-benzyl esters of the formula (I) are distinguished by a high insecticidal and acaricidal activity.

Surprisingly, the compounds of the formula (I) exhibit a considerably more powerful insecticidal and acaricidal action than compounds of analogous structure and the same type of action which are known from the state of the art.

The general formula (I) includes the various possible stereoisomers and optically active isomers, and mixtures thereof.

Preferred compounds of the formula (I) are those in which
R¹ represents hydrogen or cyano and
R² represents pentafluorophenyl, 4-fluoro-3-phenoxy-phenyl, 3-(4-fluoro-phenoxy)-phenyl or 4-fluoro-3-(4-fluoro-phenoxy)-phenyl.

In a preferred variant (a) of the preparative process for the compounds of the formula (I), 3-(2,3-dichloro-3,3-difluoro-prop-1-en-1-yl)-2,2-dimethylcyclo-propanecarboxylic acid chloride, of the formula

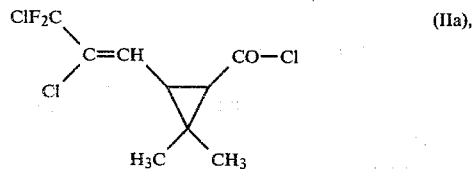

is reacted with a benzyl alcohol of the formula (III) above, in the presence of an acid acceptor and using a diluent.

In another preferred process variant (b), in particular for the preparation of compounds of the formula (I) in which R¹ represents cyano and R² represents fluorine-substituted phenoxy-phenyl, the acid chloride of the formula (IIa) above is reacted with the appropriate phenoxy-benzaldehyde of the general formula

in which
R² represents fluorine-substituted phenoxy-phenyl, and at least an equimolar amount of an alkali metal cyanide (especially sodium cyanide or potassium cyanide) in the presence of water and a water-immiscible organic solvent, and if appropriate in the presence of a catalyst.

Other reactive derivatives of the carboxylic acid of the formula (II) which may be mentioned are lower (e.g. C₁-C₄) alkyl esters thereof, which can be reacted with alcohols of the formula (II) by customary methods.

It is also possible to react alkali metal salts, alkaline earth metal salts or ammonium salts of the carboxylic acid (II) with benzyl halides, which are derived from the benzyl alcohols of the formula (III), to give compounds of the formula (I).

If, for example, pentafluorobenzyl alcohol is used as the starting substance in process variant (a) and 4-fluoro-3-(4-fluoro-phenoxy)-benzaldehyde is used as the starting substance in variant (b), the reactions in the two process variants can be outlined by the following equations:

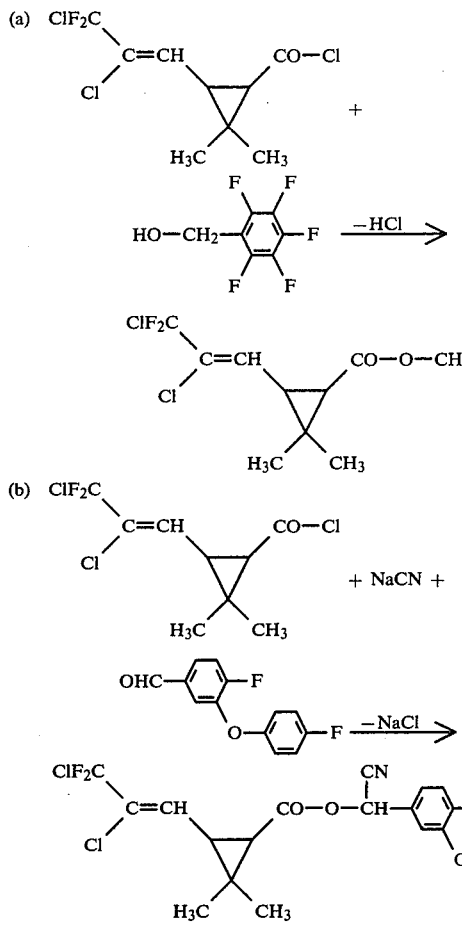

The 3-(2,3-dichloro-3,3-difluoro-prop-1-en-1-yl)-2,2-dimethyl-cyclopropanecarboxylic acid to be used as the starting compound is already known (see DE-OS (German Published Specification) No. 2,802,962 or British Pat. No. 2,000,764).

The acid chloride of the formula (IIa) is obtained from the acid in the customary manner, for example by reaction with thionyl chloride, if appropriate in the presence of a diluent, for example carbon tetrachloride, at a temperature between 10° and 100° C.

Formula (III) provides a definition of the benzyl alcohols also to be used as starting substances. Preferably, in this formula, $R^1$ and $R^2$ have those meanings which have already been mentioned as preferred in the definition of $R^1$ and $R^2$ in formula (I).

Examples of the starting compounds of the formula (III) which may be mentioned are: pentafluoro-benzyl alcohol, 4-fluoro-3-phenoxy-benzyl alcohol, 3-(4-fluorophenoxy)-benzyl alcohol, 4-fluoro-3-(4-fluoro-phenoxy)benzyl alcohol and 3-(4-fluoro-phenoxy)-α-cyano-benzyl alcohol.

The starting compounds of the formula (III) are already known (see British Pat. No. 1,078,511 and DE-OS's (German Published Specification) No. 2,621,433, U.S. Pat. No. 4,218,469, issued Aug. 19, 1980 and U.S. Pat. No. 4,199,596, issued Apr. 22, 1980.

Formula (IV) provides a definition of the phenoxybenzaldehydes which can be used as starting substances. Preferably, in this formula, $R^2$ has those meanings which have already been mentioned as preferred in the definition of $R^2$ in formula (I).

Examples which may be mentioned are: 4-fluoro-3-phenoxy-benzaldehyde, 3-(4-fluoro-phenoxy)-benzaldehyde and 4-fluoro-3-(4-fluoro-phenoxy)-benzaldehyde.

The phenoxybenzaldehydes of the formula (IV) are already known (see DE-OS's (German Published Specification) No. 2,621,433, U.S. Pat. No. 4,218,469 and U.S. Pat. No. 4,199,596, issued Apr. 22, 1980.

All variants of the process for the preparation of the compounds of the formula (I) are preferably carried out using a diluent. Possible diluents are virtually any of the inert organic solvents. These include, as preferences, aliphatic and aromatic, optionally halogenated hydrocarbons, such as pentane, hexane, heptane, cyclohexane, petroleum ether, benzene, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane; ketones, such as acetone, methyl ethyl ketone, methyl ethyl ketone, methyl isopropyl ketone and methyl isobutyl ketone; esters, such as methyl acetate and ethyl acetate; nitriles, for example acetonitrile and propionitrile; amides, for example dimethylformamide, dimethylacetamide and N-methylpyrrolidone; and dimethylsulphoxide, tetramethylene sulphone and hexamethylphosphoric acid triamide.

Variant (a) of the process according to the invention is preferably carried out in the presence of an acid acceptor. Any of the customary acid-binding agents can be used as the acid acceptor. Acid-binding agents which have proved particularly suitable are alkali metal carbonates and alcoholates, such as sodium carbonate, potassium carbonate, sodium methylate or ethylate and potassium methylate or ethylate, and furthermore aliphatic, aromatic or heterocyclic amines, for example triethylamine, trimethylamine, dimethylaniline, dimethylbenzylamine, pyridine, diazabicyclooctane, diazabicyclononane and diazabicycloundecene.

Variant (b) of the process according to the invention is carried out in the presence of water and an organic solvent which is immiscible with water, preferably one of the organic solvents mentioned above. The above-mentioned hydrocarbons are particularly suitable in this case.

Catalysts which are used in process variant (b) are preferably compounds which are suitable for transferring anions from water to organic solvents. Examples of such catalysts are benzyl-triethylammonium bisulphate, tetrabutylammonium bromide and methyltrioctylammonium chloride (Aliquat 336).

The reaction temperature can be varied within a substantial range in all the process variants. In general, the reactions are carried out between 0° and 100° C., preferably at 10° to 50° C.

The process according to the invention is in general carried out under normal pressure.

The starting substances are usually employed in equimolar amounts for carrying out the process according to the invention. An excess of one or other of the reactants provides no substantial advantages. The starting substances are brought together in suitable diluents and, if appropriate after adding an acid acceptor and/or a catalyst, the mixture is stirred until the reaction has ended.

Working up can be carried out by customary methods, for example by a procedure in which the reaction mixture is diluted, if appropriate, with water and/or a water-immiscible organic solvent, for example, toluene, the organic phase is separated off, washed with water, dried and filtered and the solvent is carefully distilled off from the filtrate under reduced pressure and at a moderately elevated temperature ("incipient distillation").

The active compounds are well tolerated by plants, have a favorable level of toxicity to warm-blooded animals, and can be used for combating arthropod pests, especially insects or acarids, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp.; *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossyppi, Brevicoryne brassicae, Cryptomyzus ribis, Doralis fabae, Doralis pomi, Eriosoma lanigerum, Hyalopterus arundinis, Macrosiphum avenae,* Myzus spp.; *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., Trichoplusia ni, *Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Cestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surfaceactive agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylenefatty alcohol ethers, for example alkylaryl polyglycol ethers, alkyl sulphonates, alkyl sulphates, aryl-sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl-acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably 0.000001 to 1% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention also provides a pesticidal composition containing as active ingredient a compound of the present invention in admixture with a solid or liquefied gaseous diluent or carrier or in admixture with a liquid diluent or carrier containing a surfaceactive agent.

The present invention also provides a method of combating pests (in particular arthropods and especially insects or acarids) which comprises applying to the pests, or to a habitat thereof, a compound of the present invention alone or in the form of a composition containing as active ingredient a compound of the present invention in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

Preparative Example

EXAMPLE 1

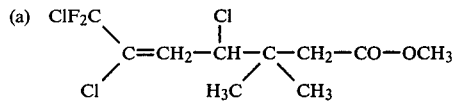

37.5 g of 3,3-dimethyl-4-pentenoic acid methyl ester, 102 g of 1,1,1,2-tetrachloro-2,2-difluoroethane, 22 g of acetonitrile, 325 mg of $FeCl_3 \cdot 6H_2O$, 255 mg of benzoin and 200 mg of dimethylamine hydrochloride were heated to 100°–120° C. in a 250 ml VA autoclave under 6 bars of nitrogen for 7 hours. Distillation of the mixture gave 3,3-dimethyl-4,6,6,7-tetrachloro-7,7-difluoro-enanthic acid methyl ester of boiling point 129°–134° C./0.7–0.9 m bar. Refractive index: $n_D^{20} = 1.4680$.

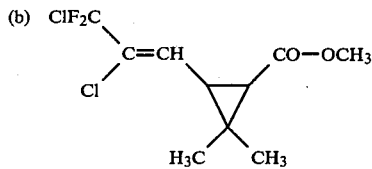

A solution of 160 g (0.462 mol) of 3,3-dimethyl-4,6,6,7-tetrachloro-7,7-difluoro-enanthic acid methyl ester was added dropwise to a solution of 183 g of 30% strength sodium methylate solution in 500 ml of methanol at room temperature in the course of 2 hours, while stirring. The mixture was subsequently stirred at room temperature for 2 hours and was then heated to 45°–50° C. for 8 hours. After cooling, some of the methanol was distilled off under reduced pressure, 500 ml of ice-water were added to the remainder of the mixture and the mixture was rendered neutral. After extraction with methylene chloride, the product phase was dried with sodium sulphate and, after distilling off the solvent, distilled under a high vacuum. 112 g of crude product of boiling point 70°–95° C./0.3 m bar were obtained, and were fractionated over a column. The pure 2,2-dimethyl-3-(2',3'-dichloro-3',3'-difluoro-1'-propenyl)-cyclopropane-1-carboxylic acid ester (isomer mixture of 3 stereoisomers) boiled at 67°–73° C./0.3 m bar.

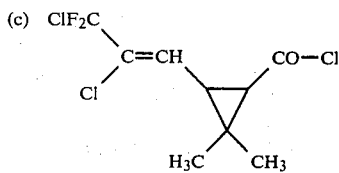

135 ml of 3 N methanolic potassium hydroxide solution were added to 27.3 g (0.1 mol) of 2,2-dimethyl-3-(2',3'-dichloro-3',3'-difluoro-1'-propanyl)-cyclopropane-1-carboxylic acid methyl ester and the mixture was stirred at room temperature for 8 hours. Ice-water was then added and the mixture was rendered acid with 130 ml of 10% strength hydrochloric acid. Extraction three times with methylene chloride gave 2,2-dimethyl-3-(2',3'-dichloro-3',3'-difluoro-1'-propenyl)-cyclopropane-1-carboxylic acid (isomer mixture), to which 30 ml of thionyl chloride were added; the mixture was then heated to 80° C. for 1 hours, whilst stirring. After distilling off the excess thionyl chloride under normal pressure, the residue was distilled under a high vacuum. 21 g of 2,2-dimethyl-3-(2',3'-dichloro-3',3'-difluoro-1'-propenyl)-cyclopropane-1-carboxylic acid chloride (isomer mixture) of boiling point 64° C./0.08 m bar were obtained.

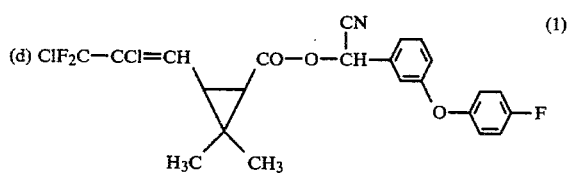
(d) (1)

3.1 g of 2,2-dimethyl-3-(2',3'-dichloro-3',3'-difluoro-1'-propenyl)-cyclopropane-1-carboxylic acid chloride were mixed with 100 ml of toluene and 2.67 g of the cyanohydrin of 3-(4'-fluorophenoxy)-benzaldehyde, 0.9 g of pyridine in 25 ml of toluene were then added dropwise at room temperature, while stirring, and the mixture was subsequently stirred at room temperature for 4 hours. 150 ml of water were then added to the reaction mixture and the organic phase was separated off and washed with 100 ml of water. The organic phase was dried with sodium sulphate and filtered, the filtrate was concentrated on a rotary evaporator and the residue was subjected to incipient distillation at 60° C. under a high vacuum (for about 1 hour). The residue weighed 4.3 g and consisted of 2,2-dimethyl-3-(2',3'-dichloro-3',3'-difluoro-1'-propenyl)-cyclopropane-1-carboxylic acid 3-(4'-fluoro-phenoxy)-α-cyanobenzyl ester with a refractive index $n_D^{20}$ of 1.5340.

The following compounds were obtained analogously:

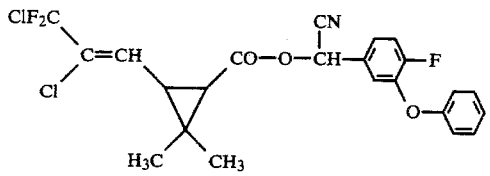
(2)

and, from the corresponding benzyl alcohols,

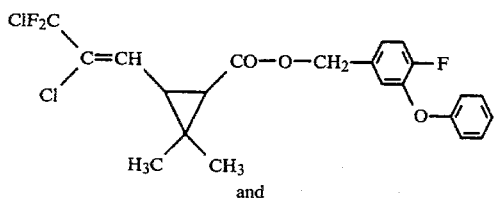
(3)
and

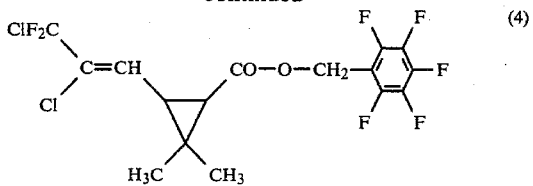
(4)

The pesticidal activity of the compounds of this invention is illustrated by the following examples wherein the compounds according to the present invention are each identified by the number (given in brackets) from Example 1:

EXAMPLE 2

Drosophila test
Solvent: 3 parts by weight of acetone
Emulsifier: 1 parts by weight of alkylaryl polyglycol ether To produce a suitable preparation of active compound, 1 parts by weight of active compound was mixed with the stated amount of solvent and the stated amount of emulsifier, and the concentrate was diluted with water to the desired concentration.

1 cm³ of the preparation of the active compound was pipetted onto a filter paper disc (7 cm diameter). The wet disc was placed over the opening of a glass vessel containing 50 vinegar flies (*Drosophila melanogaster*) and was covered with a glass plate.

After the specified periods of time, the destruction in % was determined. 100% meant that all the flies had been killed; 0% meant that none of the flies had been killed.

In this test, the following compound showed a superior activity compared with the prior art: (4).

EXAMPLE 3

Myzus test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were treated by being dipped into the preparation of active compounds of the desired concentration.

After the specified periods of time, the degree of destruction was determined as a percentage: 100% meant that all of the aphids were killed whereas 0% meant that none of the aphids were killed.

In this test, for example, the following compounds showed a superior activity compared with the prior art: (1) and (2).

EXAMPLE 4

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were treated by being dipped into the preparation of the active compound.

After the specified periods of time, the degree of destruction was determined as a percentage: 100% meant that all of the spider mites were killed whereas 0% meant that none of the spider mites were killed.

In this test, for example, the following compounds showed a superior activity compared to the prior art: (1), (2) and (3).

EXAMPLE 5

Test insect: *Agrotis segetum* (in the soil)
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil. The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

In this test, for example, the following compounds showed a superior action compared with the prior art: (1), (2), (3) and (4).

EXAMPLE 6

LT$_{100}$ test for Diptera
Test insects: *Aedes aegypti*
Number of test insects: 25
Solvent: Acetone The active compound was dissolved in the solvent at a rate of 2 g per liter. The solution so obtained was diluted with further solvent to the desired lower concentration.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. The stated number of test insects was then placed in the Petri dish and the dish was covered with a glass lid.

The condition of the test animals was continuously observed. The time which was necessary for 100% "knock-down" was determined.

In this test, for example, the following compounds showed a superior action compared with the prior art: (3), (2), (1) and (4).

EXAMPLE 7

Test with *Boophilus microplus* resistant
Solvent: 35 parts by weight of ethylene glycol monomethyl ether; 35 parts by weight of nonylphenol polyglycol ether.

To produce a suitable preparation of active compound, three parts by weight of active compound were mixed with seven parts by weight of the solvent mixture indicated above, and the concentrate thus obtained was diluted with water to the desired concentration.

10 adult *Boophilus microplus* res. were immersed for 1 minute in the active compound preparation to be tested. After transfer to plastic beakers and storage in a climatically controlled chamber, the degree of destruction was determined.

In this test, for example, the following compounds showed a superior action compared with the prior art: (2) and (3).

It will be appreciated that the instant specification and examples are set forth by way of illustration and not limitation, and that various modifications and changes may be made without departing from the spirit and scope of the present invention.

We claim:

1. A 3-(2,3-dichloro-3,3-difluoro-prop-1-en-1-yl)-2,2-dimethyl-cyclopropanecarboxylic acid fluorobenzyl ester of the formula

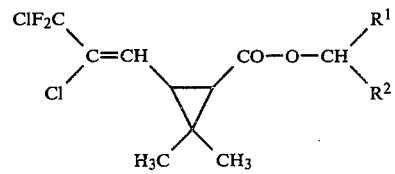

in which
R$^1$ represents hydrogen, cyano, alkyl with up to 4 carbon atoms, alkenyl with up to 4 carbon atoms or alkynyl with up to 4 carbon atoms, and
R$^2$ represents a phenyl radical which is substituted by fluorine and/or optionally fluorinesubstituted phenoxy, with the proviso that the radical R$^2$ in total contains at least one fluorine substituent.

2. A compound according to claim 1, in which
R$^1$ represents hydrogen or cyano, and
R$^2$ represents pentafluorophenyl, 4-fluoro-3-phenoxy-phenyl, 3-(4-fluoro-phenoxy)-phenyl or 4-fluoro-3-(4-fluoro-phenoxy)-phenyl.

3. A compound according to claim 1, wherein such compound is 2,2-dimethyl-3-(2',3'-dichloro-3',3'-difluoro-1'-propenyl)-cyclopropane-1-carboxylic acid 3-(4'-fluoro-phenoxy)-α-cyanobenzyl ester of the formula

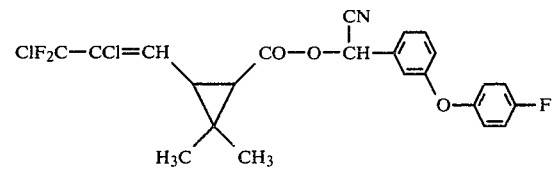

4. A compound according to claim 1, wherein such compound is 2,2-dimethyl-3-(2',3'-dichloro-3',3'-difluoro-1'-propenyl)-cyclopropane-1-carboxylic acid 4-fluoro-3-phenoxy-α-cyanobenzyl ester of the formula

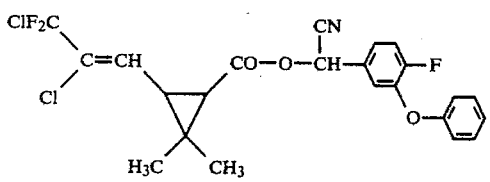

5. A compound according to claim 1, wherein such compound is 2,2-dimethyl-3-(2',3'-dichloro-3',3'-difluoro-1'-propenyl)-cyclopropane-1-carboxylic acid 4 fluoro-3-phenoxy-benzyl ester of the formula

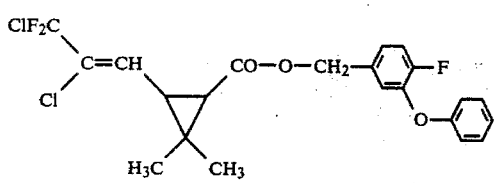

6. A compound according to claim 1, wherein such compound is 2,2-dimethyl-3-(2',3'-dichloro-3',3'-difluoro-1'-propenyl)-cyclopropane-1-carboxylic acid pentafluorobenzyl ester of the formula

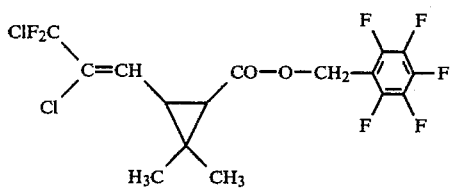

7. A pesticidal composition comprising a pesticidally effective amount of a compound according to claim 1 in admixture with a diluent.

8. A method of combating pests, comprising applying to the pests, or to a habitat thereof, a pesticidally effective amount of a compound according to claim 1.

9. The method according to claim 8, in which said compound is
2,2-dimethyl-3-(2',3'-dichloro-3',3'-difluoro-1'-propenyl)-cyclopropane-1-carboxylic acid 3-(4'-fluoro-phenoxy)-α-cyanobenzyl ester,
2,2-dimethyl-3-(2',3'-dichloro-3',3'-difluoro-1'-propenyl)-cyclopropane-1-carboxylic acid 4-fluoro-3-phenoxy-α-cyanobenzyl ester,
2,2-dimethyl-3-(2',3'-dichloro-3',3'-fluoro-1'-propenyl)-cyclopropane-1-carboxylic acid 4-fluoro-3-phenoxy-benzyl ester, or
2,2-dimethyl-3-(2',3'-dichloro-3',3'-difluoro-1'-propenyl)-cyclopropane-1-carboxylic acid pentafluorobenzyl ester.

* * * * *